United States Patent
Schuetze et al.

(10) Patent No.: US 9,903,869 B2
(45) Date of Patent: Feb. 27, 2018

(54) DEVICE AND METHOD FOR ANALYZING A SAMPLE FOR THE IDENTIFICATION OF PROSTATE TUMOURS

(71) Applicant: CellTool GmbH, Bernried (DE)

(72) Inventors: Karin Schuetze, Tutzing (DE); Waldemar Lernhardt, Obersulm-Suelzbach (DE); Raimund Schuetze, Tutzing (DE)

(73) Assignee: CellTool GmbH, Bernried (DE)

( * ) Notice: Subject to any disclaimer, the term of this patent is extended or adjusted under 35 U.S.C. 154(b) by 0 days.

(21) Appl. No.: 15/301,849

(22) PCT Filed: Apr. 7, 2015

(86) PCT No.: PCT/EP2015/057502
§ 371 (c)(1),
(2) Date: Nov. 4, 2016

(87) PCT Pub. No.: WO2015/150573
PCT Pub. Date: Oct. 8, 2015

(65) Prior Publication Data
US 2017/0122948 A1    May 4, 2017

(30) Foreign Application Priority Data
Apr. 4, 2014  (DE) ................. 10 2014 206 576

(51) Int. Cl.
*G01J 3/44* (2006.01)
*G01N 33/574* (2006.01)
*G01N 21/64* (2006.01)

(52) U.S. Cl.
CPC ....... *G01N 33/57434* (2013.01); *G01N 21/64* (2013.01)

(58) Field of Classification Search
CPC .................................................. G01N 21/64
USPC .......................................................... 356/301
See application file for complete search history.

(56) References Cited

U.S. PATENT DOCUMENTS

| 6,002,476 A | 12/1999 | Treado |
| 7,697,576 B2 | 4/2010 | Maier et al. |
| 7,755,756 B2 | 7/2010 | Stewart et al. |
| 7,767,435 B2 | 8/2010 | Chiu et al. |

(Continued)

FOREIGN PATENT DOCUMENTS

| KR | 20100002742 | 1/2010 |
| WO | 2010/131045 | 11/2010 |
| WO | 2011/154143 A1 | 12/2011 |

OTHER PUBLICATIONS

Khamis et al., "Novel Stromal Biomarkers in Human Breast Cancer Tissues Provide Evidence for the More Malignant Phenotype of Estrogen Receptor-Negative Tumors", Journal of Biomedicine and Biotechnology, vol. 2011, Article ID 723650, 7 pages.

(Continued)

*Primary Examiner* — Hina F Ayub
(74) *Attorney, Agent, or Firm* — Sand & Sebolt (57) ABSTRACT

In order to identify a prostate tumor with a Raman spectroscopy system, at least one Raman spectrum (40) of a sample is detected. The at least one Raman spectrum (40) is evaluated in order to identify a prostate tumor and/or distinguish an aggressive from a non-aggressive prostate tumor based on a characteristic pattern in the at least one Raman spectrum (40).

16 Claims, 8 Drawing Sheets

(56) References Cited

U.S. PATENT DOCUMENTS

| | | | |
|---|---|---|---|
| 7,956,996 | B2 | 6/2011 | Maier et al. |
| 8,013,991 | B2 | 9/2011 | Maier et al. |
| 8,158,957 | B2 | 4/2012 | Nelson et al. |
| 8,253,936 | B2 | 8/2012 | Cohen et al. |
| 8,395,769 | B2 | 3/2013 | Stewart et al. |
| 8,553,732 | B2 | 10/2013 | Maier et al. |
| 2005/0277816 | A1* | 12/2005 | Maier .............. A61B 5/0075 600/315 |
| 2006/0084876 | A1 | 4/2006 | Oh et al. |
| 2008/0319324 | A1* | 12/2008 | Maier .............. A61B 5/0059 600/477 |
| 2012/0316446 | A1 | 12/2012 | Vukelic |
| 2013/0052636 | A1* | 2/2013 | Verma .............. G01N 21/658 435/5 |

OTHER PUBLICATIONS

Beck, Andrew H., et al. "Systematic analysis of breast cancer morphology uncovers stromal features associated with survival." Science translational medicine 3.108 (2011): 108ra113-108ra113.

Replies to "Systematic Analysis of Breast Cancer Morphology Uncovers Stromal Features Associated with Survival."

Jia et al., "Diagnosis of Prostate Cancer Using Differentially Expressed Genes in Stroma", Cancer Research 2011; 71:2476-2487, published online Mar. 31, 2011.

Devpura et al., "Diagnosis of Prostatic Intraepithelial Neoplasia in Luminal Cells Using Raman Spectroscopy", Intraepithelial Neoplasia, p. 163-178, ISBN 978-953-307-987-5, Feb. 8, 2012.

Rachel E. Kast et al. "Emerging Technology: Applications of Raman Spectroscopy for Prostate Cancer", Cancer and Metastasis Reviews, vol. 33, No. 2-3, Feb. 9, 2014, pp. 673-693.

Matthew Tollefson et al. "Raman Spectral Imaging of Prostate Cancer: Can Raman Molecular Imaging be Used to Augment Standard Histopathology?", BJU International, vol. 106, No. 4, Aug. 1, 2010, pp. 484-488.

P Crow et al. "The Use of Raman Spectroscopy to Identify and Grade Prostatic Adenocarcinoma in Vitro", British Journal of Cancer, vol. 89, No. 1, Jul. 7, 2003, pp. 106-108.

Celltool: "BioRam", Nov. 1, 2011, Retrieved from the internet: http://celltool.de/files/celltool-bioram-flyer_en.pdf, retrieved on Jun. 22, 2015.

Bas W. D. De Jong et al.: "Discrimination between Nontumor Bladder Tissue and Tumor by Raman Spectroscopy", Analytical Chemistry, vol. 78, No. 22, Nov. 15, 2006 (Nov. 15, 2006), pp. 7761-7769 [XP055420927, US, ISSN: 0003-2700, DOI: 10.1021/ac061417b].

K. Kong et al.: "Diagnosis of tumors during tissue-conserving surgery with integrated autofluorescence and Raman scattering microscopy", Proceedings of the National Academy of Sciences, vol. 110, No. 38, Sep. 17, 2013 (Sep. 17, 2013), pp. 15189-15194 [XP055174821, ISSN: 0027-8424, DOI: 10.1073/pnas.1311289110].

* cited by examiner

DEVICE AND METHOD FOR ANALYZING A SAMPLE FOR THE IDENTIFICATION OF PROSTATE TUMOURS

FIELD OF THE INVENTION

The invention concerns devices and methods for identifying prostate tumors. The invention concerns in particular devices and methods with which a sample, for example a biopsy specimen, a tissue section, blood, urine, or ejaculate, is quantitatively evaluated in order to determine whether an aggressive or a non-aggressive prostate tumor is present.

BACKGROUND ART

Prostate cancer is one of the most common neoplastic diseases in men, and is among the types of tumors which are fatal in most male cancer patients. Timely identification of prostate tumors with determination of whether the tumor is malignant or benign is of decisive importance. Various techniques for this purpose are known. Suspected diagnoses can be established by palpation in digital rectal examination. For quantitative analysis, ultrasound examination, magnetic resonance tomography, or positron emission tomography (PET) can be used. Moreover, biomarkers such as prostate biomarkers can support the identification and differentiation of malignant prostate tumors and benign prostate tumors. Some of these biomarkers can be detected, for example, in the blood, urine, or ejaculate. In analysis of a biopsy tissue sample, a determination of whether prostate cancer is present is made based on said tissue sample. The identification of prostate tumors, and the determination of whether an aggressive tumor or non-aggressive tumor is present, is of particular importance in deciding whether further observation (so-called "active surveillance") is indicated or whether treatments such as prostatectomy, radiotherapy, hormonal therapy, or chemotherapy must be carried out.

However, the efficient and objective analysis of samples, for example blood, urine, ejaculate, biopsy specimens, or tissue sections, remains a challenge. Many of the conventional approaches for analysis of these samples are time-consuming, expensive, and often insufficiently objective.

In particular, in analysis of biopsy specimens, a frequent problem is that the specimens, particularly in the case of small prostate tumors, may contain only tissue located far from the prostate tumor. In such cases, conventional analysis methods often do not provide sufficiently reliable findings to establish where an aggressive or non-aggressive prostate tumor is present.

SUMMARY

There is a need for devices and methods for analyzing a sample by means of which prostate tumors can be identified. In particular, there is a need for devices and methods which allow objective determination of whether an aggressive or a non-aggressive prostate tumor is present based on quantitative measurement values.

According to illustrative embodiments of the invention, Raman spectroscopy is carried out in order to analyze a sample. One or a plurality of Raman spectra can be analyzed in order to obtain a fingerprint of an aggressive or non-aggressive prostate tumor detected by Raman spectroscopy based on the Raman spectrum or a site-dependent change in Raman spectra. For example, one or a plurality of Raman spectra can be analyzed in order to identify prostate tumors and/or determine their spatial distribution based on the presence or absence of specified biomolecules. The sample can be a tissue sample, for example a biopsy specimen or a tissue section.

By evaluating one or a plurality of Raman spectra, the sample can be objectively and quantitatively analyzed. A comparison with reference spectra deposited in a database can be conducted in order to determine whether a malignant or benign prostate tumor is present. Additional data can be obtained from the Raman spectra, for example on the aggressiveness or stage of the prostate tumor (so-called "staging" or "scoring").

The reference spectra can be determined from prostatectomy tissue samples, biopsy specimens of the prostate, or prostate cancer cells from cell cultures, or by measuring the Raman spectra of biomarkers. The reference spectra can include Raman spectra or characteristics of Raman spectra of the prostatic stroma. The reference spectra can be produced by comparing Raman spectra of normal prostate tissue with cancerous prostate tissue. Corresponding reference spectra can be prepared for the stroma and/or for tissues other than the prostatic stroma.

According to one embodiment, a device for identifying a prostate tumor is disclosed. The device comprises a Raman spectroscopy system for the detection of at least one Raman spectrum of a sample. The device comprises an electronic evaluation unit which is configured to identify the prostate tumor based on an evaluation of the at least one Raman spectrum.

The electronic evaluation unit can be configured to determine whether an aggressive prostate tumor or a non-aggressive prostate tumor is present by evaluating the at least one Raman spectrum. The electronic evaluation unit can be configured to evaluate the intensity of the Raman signal at at least one wavenumber which is assigned to a biomarker for an aggressive prostate tumor or a non-aggressive prostate tumor.

The electronic evaluation unit can be configured to determine whether the prostate tumor is malignant by evaluating the at least one Raman spectrum. The electronic evaluation unit can be configured to determine whether the prostate tumor is malignant by evaluating the at least one Raman spectrum, even if a Gleason score of for example 6 does not allow definitive assignment to the categories of malignant or non-malignant.

The electronic evaluation unit can be configured to determine the aggressiveness of the prostate tumor by evaluating the at least one Raman spectrum. The electronic evaluation unit can also be configured to carry out an assessment of a malignant prostate tumor (so-called "grading" of the prostate tumor) by evaluating the at least one Raman spectrum.

The electronic evaluation unit can be configured to determine the stage of the prostate tumor (so-called "staging" of the prostate tumor) by evaluating the at least one Raman spectrum.

The device can be configured to detect at least one Raman spectrum in each case at multiple sites in a tissue sample. The device can comprise at least one controllable motor in order to provide relative movement between the sample and the optical components of the Raman spectroscopy system so as to allow automatic detection of Raman spectra at multiple sites in the tissue sample. The multiple sites and the distance can also be set in a user-defined manner. The multiple sites and the distance can automatically be determined by the system, for example by means of corresponding configurations that can be implemented in hardware, software, or firmware.

The device can be configured to identify the multiple sites in such a way that one Raman spectrum in each case can be detected for individual cells in a tissue sample. Alternatively or additionally, the device can be configured to identify the multiple sites in such a way that one Raman spectrum in each case is detected for individual subcellular areas, for example cell nuclei and cytoplasm, in a tissue sample.

The device can comprise at least one controllable motor in order to provide relative movement between the sample and the optical components of the Raman spectroscopy system so as to automatically detect Raman spectra at multiple sites in the tissue sample. The multiple sites and the distance can also be determined in a user-defined manner.

The electronic evaluation unit can be configured to evaluate the Raman spectra detected at multiple sites. In particular, this allows automatic identification of changes in Raman peaks which are associated with benign or malignant prostate tumors.

The electronic evaluation unit can be configured to carry out one statistical analysis, for example a principal component analysis (PCA) or a hierarchical or non-hierarchical cluster analysis, for each of the Raman spectra detected at multiple sites.

Based on the result of the statistical analysis, the electronic evaluation unit can conduct an evaluation of whether an aggressive or a non-aggressive prostate tumor is present. The principal component analysis or cluster analysis can allow automatic differentiation of aggressive and non-aggressive prostate tumors based on the Raman spectra.

The electronic evaluation unit can be configured to detect a site-dependent change in a Raman signal from the Raman spectra detected at multiple sites in order to determine whether an aggressive or a non-aggressive prostate tumor is present. The site-dependent change in the Raman signal of at least one biomarker for aggressive prostate tumors can be detected in order to determine whether an aggressive prostate tumor or a non-aggressive prostate tumor is present. The site-dependent change in the results of the statistical analysis of the Raman spectra detected at multiple sites can be detected in order to determine whether an aggressive prostate tumor or a non-aggressive prostate tumor is present. In this manner, it can be determined from the Raman spectra as a whole whether an aggressive or a non-aggressive tumor is present. Assignment of Raman peaks to individual biomarkers is possible, but not absolutely necessary. Differentiation of aggressive and non-aggressive prostate tumors is possible in a simple manner. In particular, by analyzing a Raman spectrum or a plurality of Raman spectra which have been or are detected in tissue, urine, blood, ejaculate, or substances obtained therefrom, it can be determined whether an aggressive or a non-aggressive tumor is present.

Differentiation of aggressive and non-aggressive prostate tumors can be carried out without it being absolutely necessary to assign individual Raman peaks to biomarkers or other substances. Rather, one can determine from the Raman spectra as a whole whether an aggressive or non-aggressive prostate tumor is present. By means of a statistical analysis, e.g. PCA or cluster techniques, a pattern or a plurality of patterns in the spectrum can be used as a differentiation criterion to distinguish aggressive and non-aggressive prostate tumors. Such patterns can be defined by the position of a plurality of Raman peaks, their height, and/or the steepness of the flanks.

Alternatively or additionally, the reaction of prostate cells, stroma cells, or other components of the sample to substances produced by a prostate tumor can also be determined.

The electronic evaluation unit can be configured to determine a gradient of the local change in a spatially resolved manner. The gradient can be a gradient of an intensity, i.e. the amplitude, of a Raman peak. The gradient can be the gradient of a height or flank steepness of Raman peaks and/or combination of the peaks. The gradient can be the gradient of a position resulting from a principal component analysis or a hierarchical or non-hierarchical cluster analysis in a multidimensional data space. Based on this, an assessment of the prostate tumor can be carried out by the electronic evaluation unit. Alternatively or additionally, conclusions can be drawn as to the site of the malignant prostate tumor.

The electronic evaluation unit can be configured to determine the gradients in a spatially resolved manner.

The electronic evaluation unit can be configured to determine a site of the prostate tumor in the tissue sample or relative to the tissue sample by evaluating the Raman spectra detected at multiple sites. The electronic evaluation unit can be configured to determine the site of a malignant prostate tumor based on the local change in Raman signals even in cases where no cancer cells are contained in the tissue sample. The electronic evaluation unit can be configured to determine the site of an aggressive prostate tumor based on the local change in Raman signals even in cases where the tissue sample is a prostatic stromal tissue sample.

The electronic evaluation unit can be configured to compare the Raman spectra detected at multiple sites with stored reference spectra. The reference spectra can include Raman spectra determined in a spatially resolved manner in samples with malignant prostate tumors, samples with non-aggressive prostate tumors, and/or samples without prostate tumors.

The electronic evaluation unit can be configured to subject the Raman spectra detected at multiple sites to a statistical analysis, for example a principal component analysis or a hierarchical or non-hierarchical cluster analysis, and to compare the result with a statistical analysis of the reference spectra.

The tissue sample can be a histological section of a biopsy specimen. The biopsy specimen can be a biopsy specimen obtained by punch biopsy.

The tissue sample can be a histological section from one or more parts of a surgically removed prostate.

The device can be configured to detect a plurality of Raman spectra in a spatially resolved manner for tissue samples of each of a plurality of biopsy specimens. Raman spectra evaluated for the plurality of biopsy specimens can be used to determine whether a benign tumor or a malignant tumor is present. The Raman spectra evaluated for the plurality of biopsy specimens can be used to determine whether an aggressive tumor or a non-aggressive tumor is present.

The biopsy specimen can be a biopsy specimen of the prostatic stroma.

The sample can comprise blood, urine, or ejaculate or can be obtained from blood, urine or ejaculate. The device can be configured to determine by Raman spectroscopy whether biomolecules or biomarkers indicative of the presence of an aggressive prostate tumor are present.

The biomolecules which are identified by Raman spectroscopy can for example be DNA or proteins, i.e. genetic or molecular biomarkers, or a mixture thereof. The biomarkers can be protein biomarkers. The characteristic Raman spectra determined therefrom can be used as a "photonic fingerprint," which provides a photonic biomarker for the identification of aggressive prostate tumors. These can serve as a reference for further analyses. Assessment of such photonic fingerprints for individual biomarkers is possible, but not absolutely necessary, in order for example to differentiate aggressive and non-aggressive tumors. For example, a statistical analysis such as a principal component analysis or a cluster analysis can be used on one or a plurality of detected Raman spectra in order to determine whether the detected Raman spectrum is to be assigned to an aggressive or a non-aggressive tumor.

The electronic evaluation unit can be configured to determine the aggressiveness of the prostate tumor by evaluating the at least one Raman spectrum.

The electronic evaluation unit can be configured to determine the aggressiveness of the prostate tumor based on the detected Raman spectrum at one or a plurality of wavenumbers or wavenumber ranges. The one or a plurality of wavenumbers or wavenumber ranges can be selected from individual or multiple wavenumber groups.

A method for evaluating a sample for the identification of a prostate tumor comprises the detection of at least one Raman spectrum in the sample and identification of the prostate tumor by evaluating the at least one Raman spectrum.

The sample can be a tissue sample, for example a tissue section of a biopsy specimen obtained by punch biopsy.

The tissue sample can be a histological section from one or more parts of a surgically removed prostate.

Raman spectra can be detected at multiple sites in the tissue sample. The Raman spectra detected at multiple sites can be evaluated in order to identify the prostate tumor.

For each of the Raman spectra detected at multiple sites, a statistical analysis can be carried out, for example a principal component analysis or a hierarchical or non-hierarchical cluster analysis.

The Raman spectra can be detected at multiple subcellular sites of the cells in a tissue sample. The Raman spectra detected at multiple subcellular sites can be evaluated in order to identify the prostate tumor.

Depending on the Raman spectra detected at multiple sites, a spatially resolved change in Raman signals assigned to aggressive prostate tumors can be determined. The site-dependent changes in the results of statistical analysis of the Raman spectra detected at multiple sites can be identified in order to determine whether an aggressive prostate tumor or a non-aggressive prostate tumor is present. In this manner, it can be determined from the Raman spectra as a whole whether an aggressive or a non-aggressive tumor is present. An assessment of Raman peaks for individual biomarkers is possible, but not absolutely necessary. Differentiation of aggressive and non-aggressive prostate tumors is possible in a simple manner.

One can determine how a biomarker changes in a site-dependent manner based on the Raman spectra detected at multiple sites.

Using this method, a site of the prostate tumor in the tissue sample or relative to the tissue sample can be identified.

The aggressiveness of the prostate tumor can be determined by this method. In order to determine aggressiveness, the result of a statistical analysis of the Raman spectrum can be compared with the results of this statistical analysis for reference spectra assigned to aggressive and non-aggressive prostate tumors.

By this method, one or a plurality of "photonic fingerprints" of the sample can be obtained, which define the detected Raman intensity at a plurality N of wavenumbers, e.g. N>100 wavenumbers. Assignment of such photonic fingerprints to individual biomarkers is possible, but not absolutely necessary, for example in order to differentiate aggressive and non-aggressive tumors. For example, a statistical analysis such as a principal component analysis or a cluster analysis can be used on one or a plurality of detected Raman spectra in order to determine whether the detected Raman spectrum is to be assigned to an aggressive or a non-aggressive tumor.

The method can be automatically carried out by the device according to an embodiment.

The methods according to illustrative embodiments can be carried out far from the human or animal body. The device according to illustrative embodiments can be used for an analysis of the sample in which said analysis is carried out far from the human or animal body.

The devices and methods according to illustrative embodiments can be configured so that the production of the sample, in particular the production of a biopsy specimen or a tissue section, is not included within the scope of the claimed devices and methods.

Devices and methods according to illustrative embodiments allow the objective identification of aggressive prostate tumors and their differentiation from non-aggressive prostate tumors by means of quantitative evaluation of at least one Raman spectrum of a sample.

BRIEF DESCRIPTION OF THE FIGURES

The invention is explained in further detail below based on preferred illustrative embodiments with reference to the drawings.

DESCRIPTION OF THE ILLUSTRATIVE EMBODIMENTS

Embodiments are described with reference to the figures, in which similar reference numbers denote similar features.

The features of the various illustrative embodiments described can be combined with one another, unless this is expressly excluded in the following description.

Devices and methods according to illustrative embodiments for analyzing a sample are used to determine whether a prostate tumor is malignant. Devices and methods according to illustrative embodiments can be used for automatic assessment of a malignant prostate tumor in order to determine the aggressiveness of the tumor.

In devices and methods according to illustrative embodiments, at least one Raman spectrum of a sample is detected. The sample can for example be a tissue section or a biopsy specimen obtained by punch biopsy, a tissue section from a surgically removed prostate, or blood, urine, or ejaculate, or may be obtained therefrom. At least one Raman spectrum is evaluated in order to determine whether a malignant prostate tumor is present. Additional determinations, for example for assessment ("grading") or stage determination ("staging"), can be carried out based on one or a plurality of Raman spectra.

Figure 1:
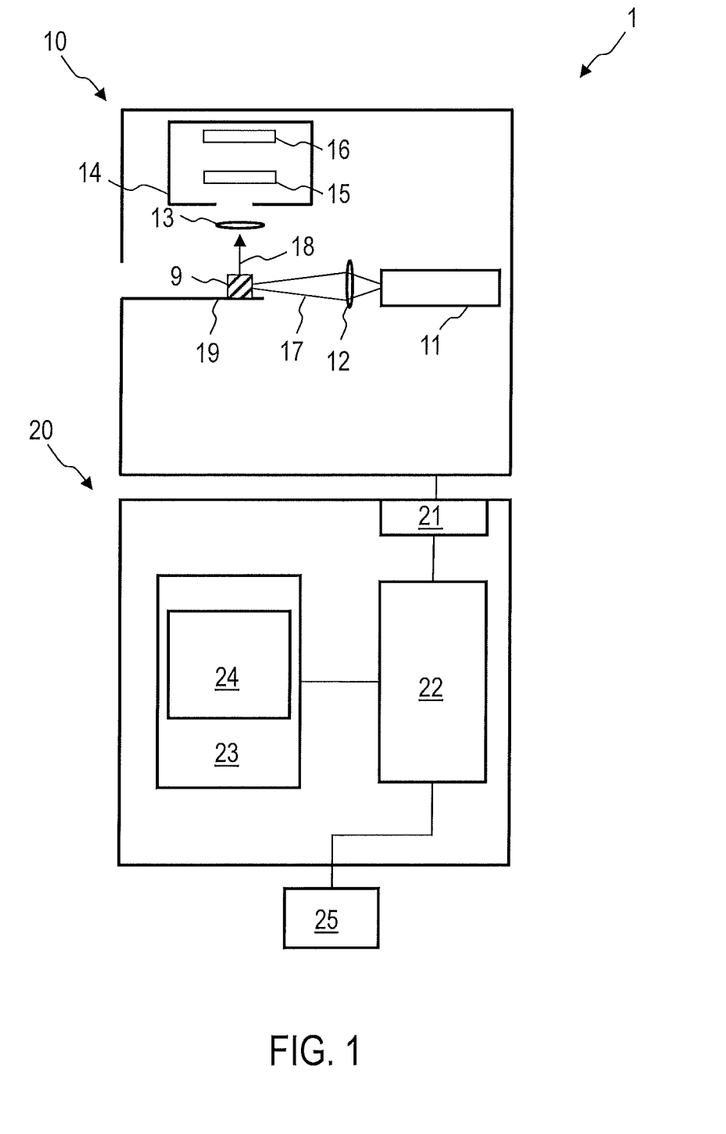
FIG. 1 shows a schematic representation of a device according to an embodiment.

FIG. 1 is a schematic representation of a device 1 according to an embodiment. The device 1 is configured to analyze a sample 9 by Raman spectroscopy in order to identify a prostate tumor, in particular a malignant prostate tumor. The corresponding identification takes place based on at least one Raman spectrum, which the device 1 detects and can automatically evaluate.

The device 1 comprises a Raman spectroscopy system 10 and an evaluation unit 20. The Raman spectroscopy system 10 is configured to detect a Raman spectrum of the sample 9. The sample 9 can be obtained, for example, from blood, urine, ejaculate, a biopsy specimen, or a tissue section, with the production of the sample in particular by punch biopsy or other removal of material not falling within the subject matter of the methods according to the illustrative embodiments.

The sample 9 can contain prostatic stromal cells. The sample 9 can also contain prostatic cells.

The Raman spectroscopy system 10 comprises a light source 11, which in particular can be a laser. The light source 11 is configured to emit an excitation beam 17. A Raman spectrometer 14 receives at the sample 9 light 18 scattered by Stokes processes and/or anti-Stokes processes. The Raman spectrometer 14 can comprise a diffractive element 15 and an image sensor 16 in order to detect the Raman spectrum of the sample 9. The Raman spectroscopy system 10 per se can comprise further elements in a known manner, for example focussing optical elements 12, 13, which can be configured as lenses, and/or screens.

The device 1 comprises an evaluation unit 20. The evaluation unit 20 can be a computer or comprise a computer. The evaluation unit 20 is coupled to the Raman spectroscopy system 10. The evaluation unit 20 can control the detection of the Raman spectrum by the Raman spectroscopy system 10. The evaluation unit 20 can control the Raman spectroscopy system 10 in such a way that Raman spectra can be detected at multiple sites in the sample 9 in a spatially resolved manner.

The evaluation unit 20 has an interface 21 for receiving data from the image sensor 16 of the Raman spectroscopy system 10. The evaluation unit has an integrated semiconductor circuit 22, which can comprise a processor or controller and is configured to evaluate the detected Raman spectrum for determination purposes. The integrated semiconductor circuit 22 is configured to determine whether a malignant prostate tumor is present based on the at least one Raman spectrum.

As will be described in further detail with reference to FIGS. 2 through 15, the integrated semiconductor circuit 22 can be configured to ascertain the presence or absence of specified Raman peaks or determine the spectral weight of Raman peaks that are associated with malignant prostate tumors. The integrated semiconductor circuit 22 can, for example, be configured to quantitatively determine whether and in what amount biomarkers for a malignant prostate tumor are present by evaluating the at least one Raman spectrum. The integrated semiconductor circuit 22 can be configured for a tissue sample to determine local changes, and in particular local gradients, of Raman signals assigned to malignant prostate tumors. Characteristic site-dependent changes in Raman spectra assigned to an aggressive prostate tumor can be deposited in a database. The site-dependent change in the Raman signal for which data are deposited in the database can indicate a change in the Raman signal in the prostatic stroma.

The Raman peaks evaluated by the integrated semiconductor circuit 22 can be assigned to molecular or genetic biomarkers. The Raman peaks evaluated by the integrated semiconductor circuit 22 can also be assigned to protein biomarkers.

Examples of biomarkers for identifying the aggressiveness of prostate tumors are carboxypeptidase A3 (CPA3), annexin 3 (ANXA 3), sarcosine, and/or PSA. The biomarkers can be selected from the group composed of AMACR, FOLH1 (PSMA), PTEN, PCA3, ERG3, and PSA. By means of devices and methods, a biomarker or a plurality of biomarkers selected from a group composed of AMACR, FOLH1 (PSMA), PTEN, PCA3, ERG3 and PSA can be identified by Raman spectroscopy.

The device 1 can be configured to determine the aggressiveness and optionally also the spatial distribution of such biomarkers. Some of the biomarkers may occur more strongly in the vicinity of a malignant prostate tumor, while other biomarkers occur more strongly at a distance from a malignant prostate tumor than in the immediate vicinity of the malignant prostate tumor.

The integrated semiconductor circuit 22 can process detected Raman spectra in various ways. For example, statistical methods, e.g. principal component analysis, can be used. Other statistical methods, for example hierarchical cluster analysis, can be used to assess whether a Raman spectrum as a whole is to be assigned to an aggressive or a non-aggressive prostate tumor. In addition, or alternatively, Raman spectra or the site-dependent change in at least individual Raman peaks can be compared with reference data in order to determine whether an aggressive prostate tumor is present. Determination of the gradients is not limited to the intensity of individual Raman peaks, but can also be carried out for example for the distance of a data point in an N-dimensional data space of a principal component analysis from the area in the N-dimensional data space to which an aggressive prostate tumor is assigned. The corresponding processing can also be automatically carried out by the integrated semiconductor circuit 22.

The evaluation unit 20 can comprise a storage unit 23 in which reference data 24 are deposited which can be used by the integrated semiconductor circuit 22 in evaluating the Raman spectrum.

The evaluation unit 20 can comprise an optical and/or acoustic output unit 25 by means of which data are output depending on the analysis of the at least one Raman spectrum which indicates whether an aggressive prostate tumor is present. An assessment of the aggressiveness of the prostate tumor can be output. Data on the stage of the prostate cancer can also be output.

Although the evaluation device 20 and the Raman spectroscopy system 10 are schematically shown in FIG. 1 as separate units, the functions of the evaluation unit 20 can also be integrated into a housing of the Raman spectroscopy system 10. The Raman spectroscopy system 10 and the evaluation device 20 can be configured as mobile units, and in particular as portable units.

Figure 2:
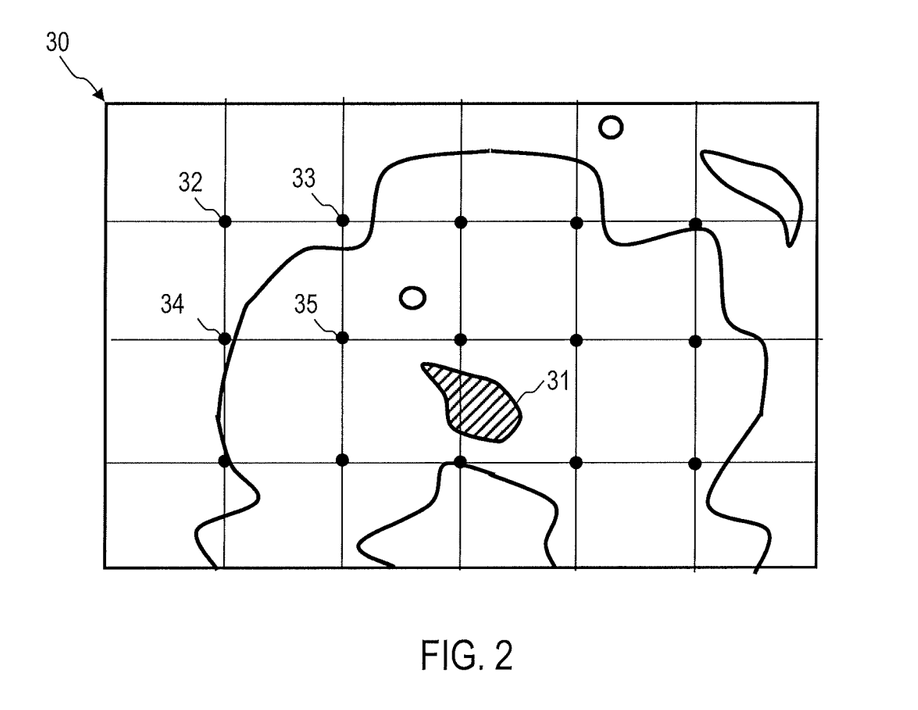
FIG. 2 shows the spatially resolved detection of Raman spectra of a sample according to an embodiment.

FIG. 2 shows a schematic diagram of a tissue sample 30. The tissue sample is shown as a tissue section. However, the techniques described can also be used on tissue samples having a different geometry, for example on biopsy specimens obtained by punch biopsy. A malignant tumor 31, which is shown only schematically, can be present. The tissue sample 30 can contain prostatic stromal cells. For the evaluation techniques described in particular, it is not necessary for tumor cells themselves to be contained in the tissue sample 30.

At least one Raman spectrum in each case can be detected in a plurality of areas shown as points or solid circles. In order to improve the statistics, a plurality of Raman spectra can also be detected at each of the points. Signal detection and relative movement between a slide and optical components of the Raman spectroscopy system can be automatically controlled by the evaluation unit 20. For example, Raman spectra can be detected in each of a plurality of small areas separated from one another 32-35.

Although FIG. 2 schematically shows a regular arrangement of points at which the Raman spectra are detected, detection can also be carried out with an irregular arrangement of points. Various patterns of points can be defined for which Raman spectroscopy is to be carried out in each case. At least some of the points 32-35 can also be established in a user-defined manner. The evaluation unit 20 can comprise a corresponding input interface, which allows user-defined determination of the points at each of which a Raman spectrum is to be detected.

Spatially resolved detection of the Raman spectra can be carried out with greater distances. According to illustrative embodiments, however, spatially resolved detection of at least two Raman spectra can be carried out in subcellular structures. At least two Raman spectra can be detected in different subcellular areas, for example for cell nuclei and cytoplasm, in a tissue sample and can be evaluated by the evaluation unit 20.

The detected Raman spectra can be evaluated in various ways. For example, a statistical analysis, e.g. a principal component analysis or a hierarchical cluster analysis, can be carried out for each of the Raman spectra. In this manner, an assessment can be conducted as to whether a Raman spectrum or the plurality of detected Raman spectra are to be assigned to an aggressive or a non-aggressive prostate tumor. Assignment of individual Raman peaks or specified spectral patterns to biomarkers can be carried out, but this is not obligatory.

The evaluation unit 20 can be configured to determine from the Raman spectrum as a whole whether an aggressive or non-aggressive prostate tumor is present. By means of statistical analysis, e.g. PCA or cluster techniques, a pattern or a plurality of patterns in the spectrum can be used as a differentiation criterion for distinguishing aggressive and non-aggressive prostate tumors. Such patterns can be defined by the position of a plurality of Raman peaks, their heights, and/or the steepness of the flanks.

Figure 3:
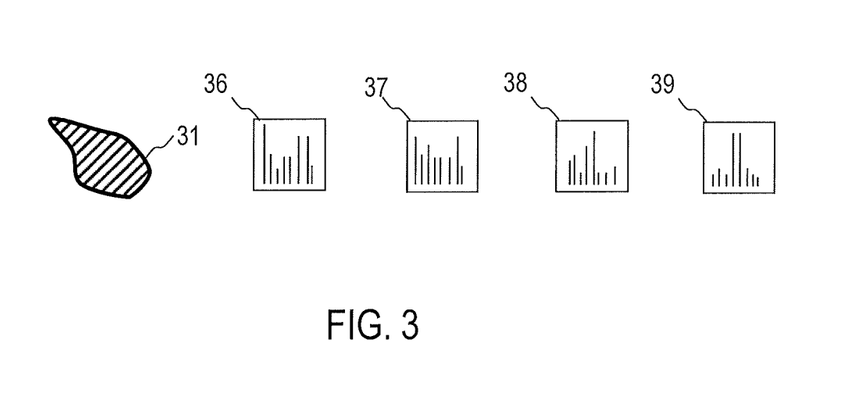
FIG. 3 shows the spatially resolved detection of Raman spectra of a sample according to an embodiment.

FIG. 3 shows as an example the evaluation of Raman spectra 36-39 for the identification and optional determination of the aggressiveness of prostate tumors. The Raman spectra 36-39 can be detected at various sites. Moreover, the position relative to the tumor 31 need not be previously known. Depending on the site, changes occur in the Raman spectra 36-39 from which conclusions can be drawn as to the presence of an aggressive or non-aggressive prostate tumor.

Figure 4:
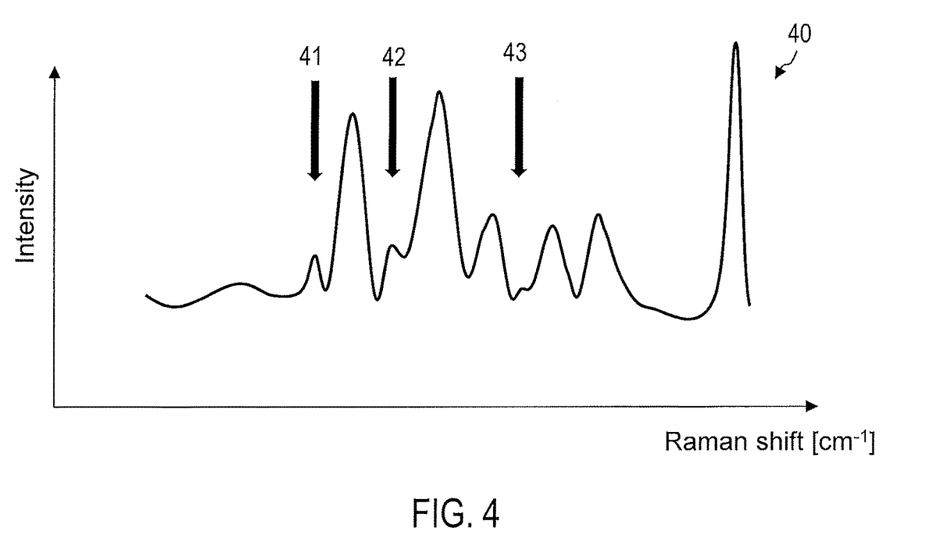
FIG. 4 shows an illustrative Raman spectrum which is evaluated by a device according to an embodiment.

FIG. 4 shows an illustrative Raman spectrum 40 which was detected in the sample 9 by the device 1. For example, the device 1 can detect the Raman spectrum 40 at a point 33 of the tissue sample 30.

The evaluation unit 20 can automatically identify a Raman peak or a plurality of Raman peaks 41-43 which are characteristic of prostate cancer. The evaluation unit 20 can be configured to identify a wavenumber range characteristic of prostate cancer or a plurality of wavenumber ranges with Raman peaks 41-43 characteristic of prostate cancer. One or a plurality of the Raman peaks 41-43 can be assigned to a biomarker for aggressive prostate tumors.

The evaluation unit 20 can, alternatively or additionally, automatically determine characteristic patterns of one or a plurality of Raman spectra 41-43. The wavenumbers at which Raman peaks are located, the peak height, the flank steepness, the distances between the peaks, and/or combinations of peaks in one or a plurality of Raman spectra 41-43 can be identified in order to determine whether an aggressive or a non-aggressive prostate tumor is present and/or to identify a prostate tumor.

It can be determined whether prostate cancer is present based on the presence and optionally the intensity of the Raman signal at the Raman peaks 41-43 which are characteristic of prostate cancer. The evaluation device 20 can assess the prostate cancer in order to determine its aggressiveness based on the intensity of the Raman signal at one or a plurality of the Raman peaks 41-43.

The Raman peaks shown schematically in FIG. 4 need not be individually identified. In particular, by means of the evaluation device 20, a statistical analysis can be carried out on the Raman spectrum as a whole in order to determine whether the Raman spectrum is to be assigned to an aggressive or a non-aggressive prostate tumor.

A plurality of Raman spectra can also be detected in the sample 9. A comparison of the various Raman spectra can be used to determine whether a malignant prostate tumor is present and/or to assess the aggressiveness of the malignant prostate tumor.

Figure 5:
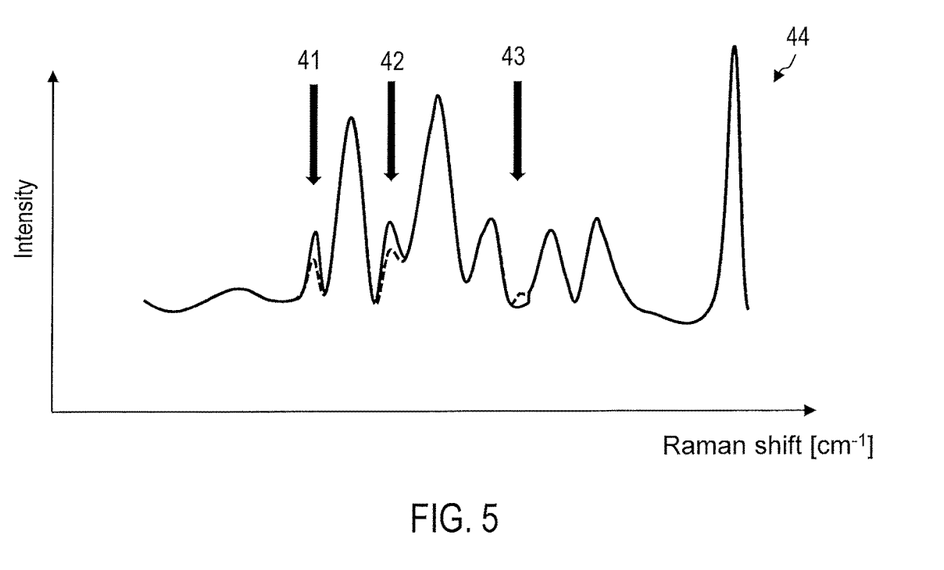
FIG. 5 shows a further illustrative Raman spectrum which is evaluated by a device according to an embodiment.

FIG. 5 shows as an example a further Raman spectrum 44, which is detected at a different site of the sample 9 than the Raman spectrum 40. The Raman spectrum 40 is also indicated in FIG. 5 by broken lines for comparison purposes.

For example, the further Raman spectrum 44 can be detected at a site 35 which is closer to the tumor than the site 33 at which the Raman spectrum 40 was detected. If the position of the prostate tumor, or even whether it is present, is not previously known, it can still be determined whether a malignant prostate tumor is present based on a comparison of the further Raman spectrum 44 at the site 35 and the Raman spectrum 40 at the site 33. It can also be determined in which direction the tumor is positioned relative to the sites 33, 35.

The intensity of the Raman signal and/or the spectral weight of the Raman peaks 41-43 can be different in the Raman spectrum 44 from the intensity and/or the spectral weight in the Raman spectrum 40. For example, the intensity of the signal at one or a plurality of Raman peaks 41, 42 can increase with decreasing distance from the site of the malignant prostate tumor if the corresponding biomarker is more strongly present in the immediate vicinity of the prostate tumor than at sites farther away. The intensity of the signal at one or a plurality of further Raman peaks 43 can decrease with decreasing distance from the site of the malignant prostate tumor if the corresponding biomarker is less strongly present in the immediate vicinity of the prostate tumor than at sites farther away.

The gradient of the Raman peaks 41-43 need not be individually determined. In particular, by means of the evaluation device 20, the Raman spectrum as a whole can be subjected to a statistical analysis in order to determine whether the Raman spectrum is to be assigned to an aggressive or a non-aggressive prostate tumor. As will be described in further detail below, for example, an assessment of Raman spectra assigned to aggressive or non-aggressive prostate tumors can be automatically carried out by the device based on the results of a statistical analysis, without it being necessary for this purpose for the individual Raman peaks 41-43 to be known in advance.

Figure 6:
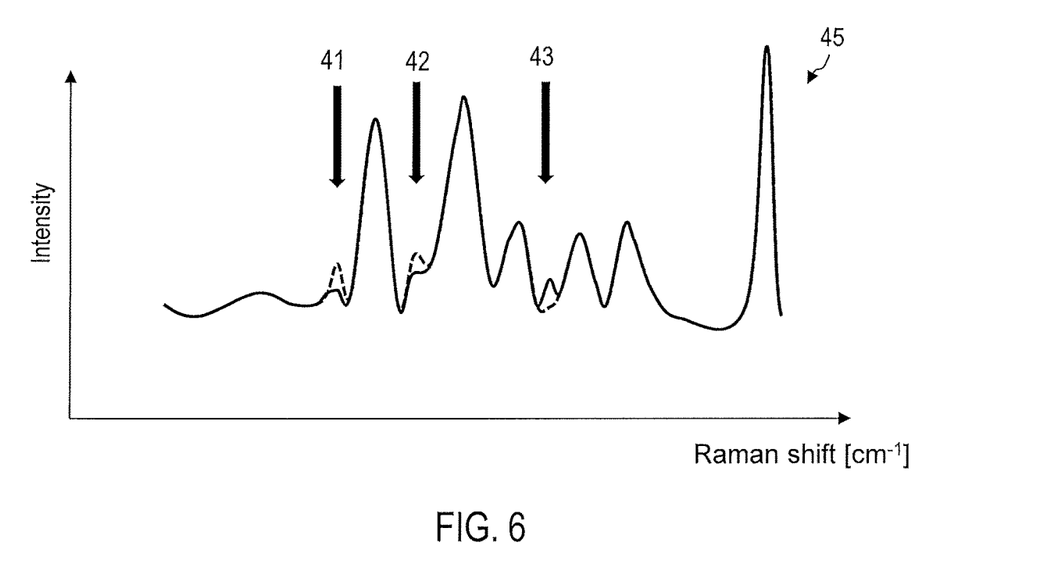
FIG. 6 shows a further illustrative Raman spectrum which is evaluated by a device according to an embodiment.

FIG. 6 shows as an example a further Raman spectrum 45 which is detected at a different site in the sample 9 than the Raman spectrum 40. The Raman spectrum 40 is also indicated by broken lines for comparison purposes.

For example, the further Raman spectrum 45 can be detected at a site 32 that lies farther away from the tumor than the site 33 at which the Raman spectrum 40 was detected. Even if the position of the prostate tumor or even whether it is present is not known in advance, it can be determined whether a malignant prostate tumor is present based on a comparison of the further Raman spectrum 45 at the site 32 and the Raman spectrum 40 at the site 33. It can also be determined in which direction the tumor is located relative to the sites 33, 35.

The intensity of the Raman signal and/or the spectral weight of the Raman peaks 41-43 can be different in the Raman spectrum 45 than the intensity and/or the spectral weight in the Raman spectrum 40. For example, the intensity of the signal at one or a plurality of Raman peaks 41, 42 can decrease with increasing distance from the site of the malignant prostate tumor if the corresponding biomarker is more strongly present in the immediate vicinity of the prostate tumor than at sites farther away. The intensity of the signal at one or a plurality of further Raman peaks 43 can increase with increasing distance from the site of the malignant prostate tumor if the corresponding biomarker is less strongly present in the immediate vicinity of the prostate tumor than at sites farther away.

The gradient of the Raman peaks 41-43 need not be individually determined. In particular, the evaluation device 20 can subject the Raman spectrum as a whole to a statistical analysis in order to determine whether the Raman spectrum is to be assigned to an aggressive or a non-aggressive prostate tumor. As will be described in greater detail below, for example, assignment of Raman spectra to aggressive or non-aggressive prostate tumors based on the results of a statistical analysis can be automatically carried out by the device, without requiring that the individual Raman peaks 41-43 be known in advance prior to conducting the measurement.

The data of a plurality of Raman spectra 40, 44, 45 can be combined in order to obtain data on the presence of a malignant prostate tumor or its aggressiveness.

In some illustrative embodiments, a local gradient of the intensity of the Raman signal can be determined at one or a plurality of the Raman peaks 41-43 characteristic of a malignant prostate tumor. For this purpose, the gradient of the intensity or the spectral weight of the Raman peaks in one, two, or three dimensions can be calculated for each of a plurality of points. Generally speaking, determination of the gradients can be carried out in n dimensions, where n can be greater than or equal to one.

The gradient can also be based on the result of further analysis of the Raman spectra. For example, by means of a statistical evaluation, each Raman spectrum can be assigned to a point in an N-dimensional data space, wherein $N \gg 1$, e.g. $N > 100$. The N-dimensional data space can be the data space spanned in a principal component analysis by the various principal components. One can determine from reference spectra in which areas of the N-dimensional data space Raman spectra are arranged in clusters for aggressive prostate tumors and in which other areas of the N-dimensional data space Raman spectra are arranged in clusters for non-aggressive prostate tumors.

The site-dependent change in Raman spectra can involve the site-dependent occurrence of further Raman peaks which can indicate the presence of further biomolecules, depending on the distance from the tumor, as well as the aggressiveness or non-aggressiveness of the tumor. Raman peaks can also disappear site-dependently (i.e. in a site-dependent process), which can also allow conclusions to be drawn as to the aggressiveness or non-aggressiveness of the tumor. The site-dependent change in Raman spectra can cause a shift in the point which, in the corresponding Raman spectrum in an N-dimensional data space, can be $N \gg 1$, e.g. $N > 100$. The N-dimensional data space can be the spanned data space in a principal component analysis of the various principal components.

In order to determine whether a Raman spectrum indicates an aggressive or a non-aggressive prostate tumor, the evaluation device 20 can thus be configured to carry out a principal component analysis, a cluster analysis, or another statistical analysis of at least one Raman spectrum. The evaluation unit 20 can be configured to quantitatively determine by statistical analysis whether the Raman spectrum belongs to a cluster or an area of the spanned data space in the principal component analysis to which the Raman spectra of aggressive prostate tumors are assigned. The evaluation unit 20 can also be configured to quantitatively determine by statistical analysis whether the Raman spectrum belongs to a cluster or an area of the spanned data space in the principal component analysis to which the Raman spectra of non-aggressive prostate tumors are assigned.

Figure 7:
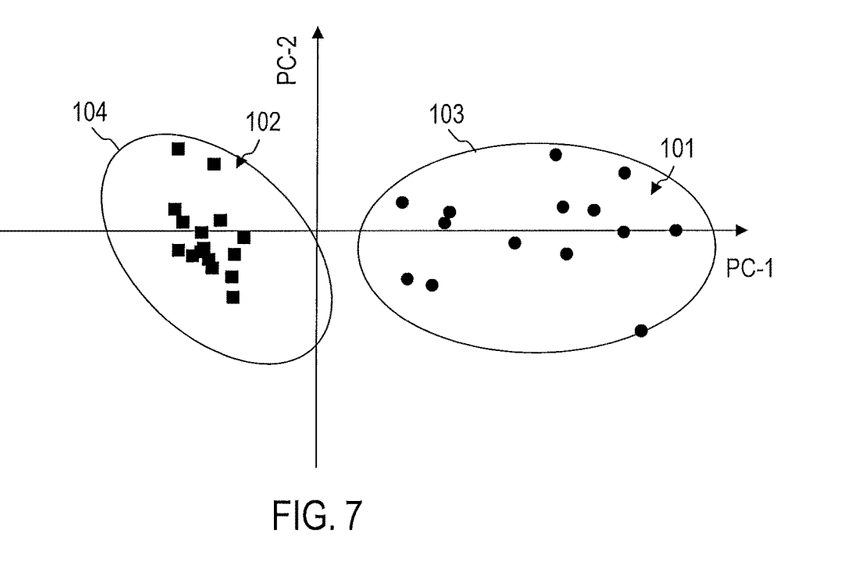
FIG. 7 shows processing of detected Raman spectra by a device according to an embodiment.

FIG. 7 shows the results of a principal component analysis for aggressive and non-aggressive prostate tumors. In the principal component analysis, the respectively detected Raman spectra can be evaluated at a plurality of $N \gg 1$, e.g. $N > 100$, Raman wavenumbers. The N-dimensional vector corresponding to the Raman intensities at the N Raman wavenumbers defines a point in an N-dimensional data space.

In the principal component analysis (PCA), a coordinate transformation in the N-dimensional data space is determined in such a way that the various clusters or groups of Raman spectra in the transformed coordinate system differ sharply along one or a plurality of the coordinate axes. These coordinate axes define the principal components. The first principal component PC-1 typically defines the axis with the sharpest differences between the different groups of Raman spectra.

FIG. 7 shows how the data points 101 corresponding to the Raman spectra of aggressive prostate tumors are separated from the data points 102 corresponding to Raman spectra of non-aggressive prostate tumors along the principal component axis PC-1.

Because of this separation occurring in the principal component analysis, it can be determined from a Raman spectrum of a sample or a plurality of Raman spectra of the sample whether these spectra are to be assigned to an aggressive or non-aggressive prostate tumor. For this purpose, each Raman spectrum can be scanned at the respective N Raman wavenumbers and then projected in the plane or the space spanned by the principal component axes of the lowest orders. For example, based on the PC-1 component, i.e. the first principal component, which shows the sharpest differences between the Raman spectra of aggressive and non-aggressive prostate tumors, it can be determined whether an aggressive or a non-aggressive prostate tumor is present. Alternatively or additionally, it can be determined whether an aggressive or a non-aggressive prostate tumor is present based on the second principal component PC-2 or another low principal component.

It should be noted that the determination of whether the Raman spectrum is characteristic of an aggressive or a non-aggressive prostate tumor can be carried out based not on individual Raman peaks, but on a plurality of Raman intensities distributed evenly or unevenly over the Raman spectra at a plurality of Raman wavenumbers. By means of the principal component analysis, or other statistical methods such as hierarchical or non-hierarchical cluster analyses, one can thus take advantage of the fact that the Raman spectrum as a whole shows characteristics that are indicative of an aggressive or non-aggressive prostate tumor and can thus serve as a "photonic fingerprint."

By means of a statistical analysis such as the principal component analysis or the cluster analysis, explained in further detail below, it can determined whether the pattern of Raman peaks contained in the Raman spectrum is characteristic of an aggressive or a non-aggressive prostate tumor. Alternatively or additionally, it can be determined whether the pattern of Raman peaks contained in the Raman spectrum is characteristic of the presence of a prostate tumor.

The pattern in a Raman spectrum can be defined by one or a plurality of parameters selected from the group composed of the wavenumbers at which the Raman peaks are located, the peak heights, the flank steepness of the peaks, the distances between the peaks, and/or combinations of peaks in one or a plurality of Raman spectra.

For evaluation of one or a plurality of Raman spectra detected in a sample, one can determine whether these peak(s) are situated in a space, according to a principal component analysis, in an area 103 assigned to aggressive prostate tumors or in another area 104 assigned to non-aggressive prostate tumors.

Figure 8:
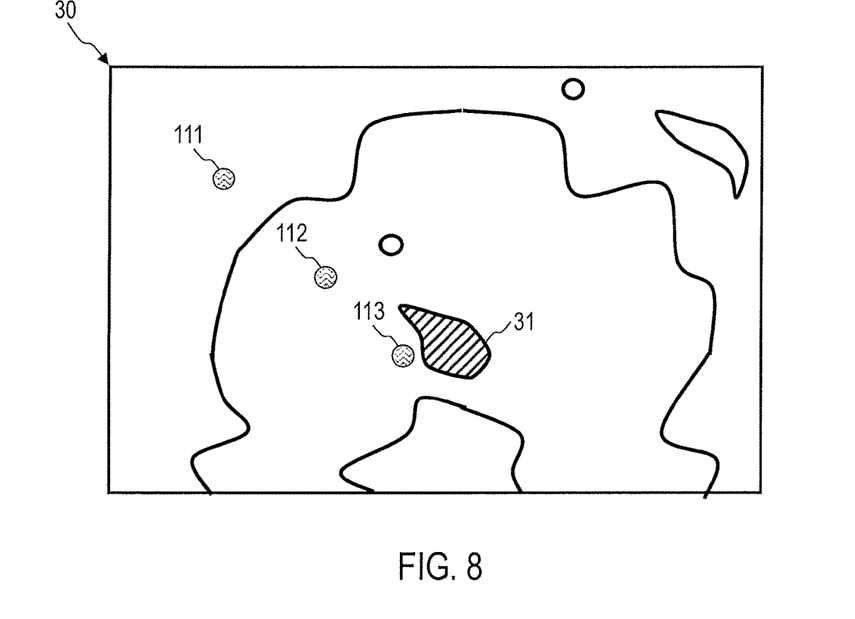
FIG. 8 shows a sample analyzed by a device according to an embodiment in order to illustrate the functioning of the device.

FIG. 8 shows a sample 30 of a prostate tumor 31. In a plurality of regions 111, 112, 113, one or preferably a plurality of Raman spectra respectively are detected for evaluation of the sample 30 by the device 1. One, a plurality, or all of the regions 111, 112, 113 can also be located in the prostatic stroma.

Each of the detected Raman spectra can be subjected to a statistical analysis by the evaluation unit of the device 1. For example, the Raman spectra can be evaluated at a plurality N of Raman wavenumbers. The vectors containing the N Raman intensities at the N Raman wavenumbers, where N>>1, can be projected by coordinate transformation in the data space with principal component axes defined based on reference spectra of aggressive and non-aggressive prostate tumors, with the lowest principal component(s) showing the clearest distinction between aggressive and non-aggressive prostate tumors.

Figure 9:
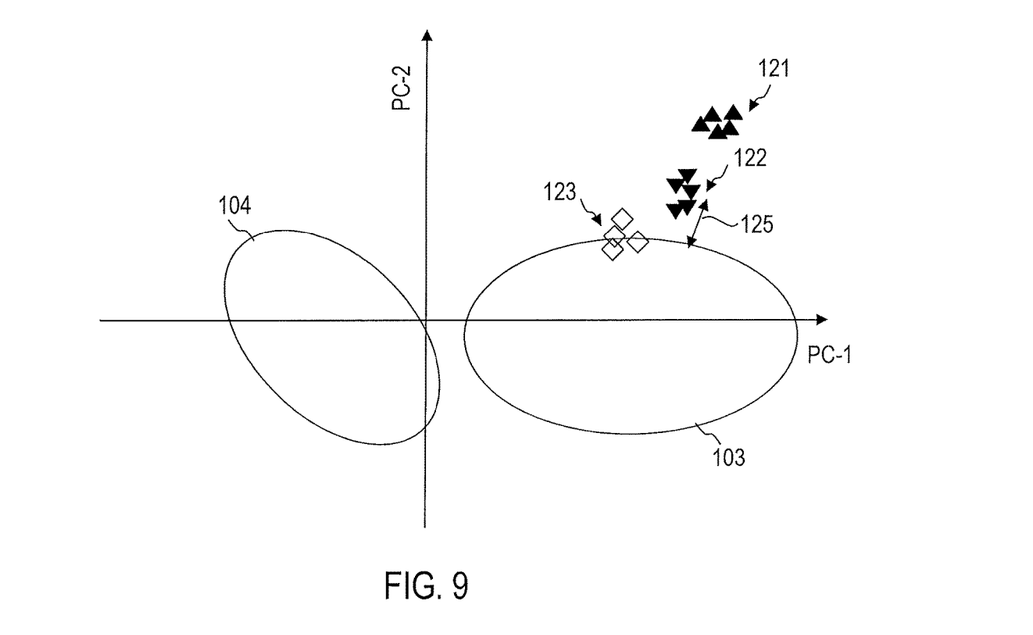
FIG. 9 shows processing of detected Raman spectra by a device according to an embodiment.

FIG. 9 shows an example of the results of such an evaluation conducted by the device 1.

Data points 121 obtained in the data space of the principal component analysis for Raman spectra detected in a region 111 do not necessarily have to lie in or directly at one of the areas 103, 104 assigned to aggressive and non-aggressive prostate tumor tissue. Based on proximity to or an overlap with one of the areas 103, 104, however, an indication of the presence of an aggressive or non-aggressive prostate tumor can be obtained, even if the region 111 is located in the stroma.

Data points 122 obtained in the data space of the principal component analysis for Raman spectra detected in a region 112 do not necessarily have to lie in or directly at one of the areas 103, 104 assigned to aggressive and non-aggressive prostate tumor tissue. Based on proximity to or an overlap with one of the areas 103, 104, however, an indication of the presence of an aggressive or non-aggressive prostate tumor can be obtained, even if the region 112 is located in the stroma. Based on the fact that the data points 122 are at a distance 125 from the area 103 which is less than a distance of the data points 121 from the area 103, it can be concluded that the region 112 is closer to an aggressive prostate tumor than the region 111. This can be used for systematic determination of the location of the prostate tumor, even if the Raman spectra were not detected in a prostate tumor cell per se.

The distances between the data points 121, 122 and the area 103 can be determined by a wide variety of methods. For example, the focus of the data points 121 or 122 can be identified, and the distance thereof from the focus of the area 103 can then be determined. The focus of the data points 121 or 122 can be identified, and the distance thereof from the edge of the area 103 can then be determined. The distances of each of the data points 121 or 122 from the focus or edge of the area 103 can be determined, and the distances can then be averaged. Accordingly, distances from the area 104, which is assigned to non-aggressive prostate tumors, can also be determined. In this case, the distance from an edge of one of the areas 103, 104 is defined respectively as the minimum distance in the data space between the corresponding data point and all points in the data space lying at the edge of the corresponding areas 103, 104.

Data points 123 obtained in the data space of the principal component analysis for Raman spectra detected in a region 113 can lie in or directly at one of the areas 103, 104 assigned to aggressive and non-aggressive prostate tumor tissue. Based on the overlap, it can be determined that the region 113 is situated close to or overlapping an aggressive prostate tumor. Based on the fact that the data points 123 are at a distance from the area 103 which is less than a distance of the data points 121 from the area 103 and a distance 125 of the data points 122 from the area 103, it can be concluded that the region 113 is closer to an aggressive prostate tumor than the regions 111 and 112. This can be used for systematic determination of the location of the prostate tumor, even if the Raman spectra were not detected in a prostate tumor cell per se.

Alternatively or additionally to the principal component analysis, hierarchical or non-hierarchical cluster analyses can also be used respectively to determine whether a Raman spectrum as a whole shows greater similarity to the Raman spectra of reference samples containing aggressive prostate tumors or the Raman spectra of reference samples not containing aggressive prostate tumors.

In such cluster analyses, spectra can be grouped together or clustered based on a measure of similarity. Various measures of similarity can be used. For example, a cosine distance can be used to define a distance metric for Raman spectra.

In hierarchical cluster analyses, a tree of Raman spectra can be set up in which assessment of Raman spectra at the same or different nodes depends on the respective measure of similarity.

In hierarchical cluster analyses, after setting up a tree of Raman spectra, this tree can be divided into two or more subtrees. These subtrees can be assigned, for example, to aggressive prostate tumors, non-aggressive prostate tumors, or tumor-free tissue.

Setting up of the tree of reference spectra need not be carried out in every evaluation of detected Raman spectra. Rather, the corresponding tree of Raman spectra can be set up based on a plurality of reference spectra which were assigned to aggressive or non-aggressive prostate tumors. In an evaluation of one or a plurality of Raman spectra detected in a sample, one can respectively determine in which subtree or which nodes the corresponding Raman spectra are to be classified based on the measure of distance. In this manner, the Raman spectrum detected for the sample can be assigned to an aggressive or non-aggressive prostate tumor or a sample not containing a prostate tumor.

Figure 10:
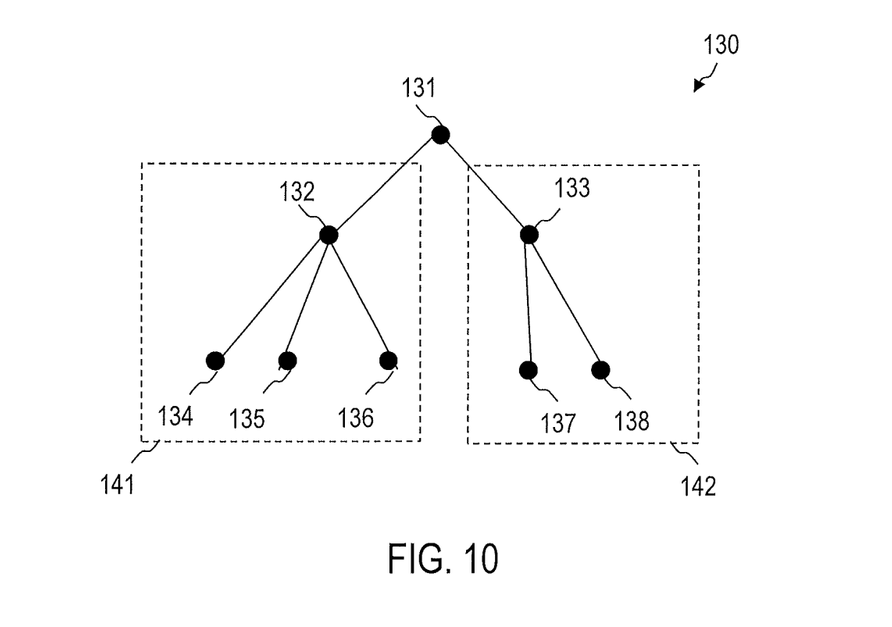
FIG. 10 shows processing of detected Raman spectra by a device according to an embodiment.

FIG. 10 schematically illustrates the functioning of the evaluation unit of the device 1 in such a statistical evaluation, which comprises a cluster analysis.

By evaluation of a plurality of reference spectra, a tree 130 of Raman spectra is created either by the evaluation unit of the device 1 itself or also far from the device 1. The tree 130 contains a plurality of nodes 131-138. Raman spectra are assigned to the nodes 131-138 based on a measure of similarity, which for example can be based on a cosine distance.

The tree 130 can have a first subtree 141 assigned to aggressive prostate tumors. The tree 130 can also have a second subtree 142 assigned to non-aggressive prostate tumors.

In evaluation of a Raman spectrum or a plurality of Raman spectra detected in a sample 30, the evaluation unit 20 of the device 1 can calculate, based in each case on the distance measurement, to which of the leaf nodes 134-138 and/or inner nodes 132, 133 of the tree 130 the corresponding Raman spectrum is to be assigned. In this manner, Raman spectra can be assigned to aggressive or non-aggressive prostate tumors even without prior knowledge of individually relevant wavenumbers. For example, Raman spectra that were detected in the stroma of a prostate with an aggressive tumor can be assigned to at least one of the various leaf nodes 134-138. For example, Raman spectra detected in the stroma of a prostate with a non-aggressive tumor can be assigned to at least one more of the various nodes 134-138.

The techniques described with reference to FIGS. 7 and 9, 10 can be used not only for samples that are tissue sections or punch biopsy specimens, but also for samples that are urine, sperm, or blood or are obtained therefrom.

Figure 11:
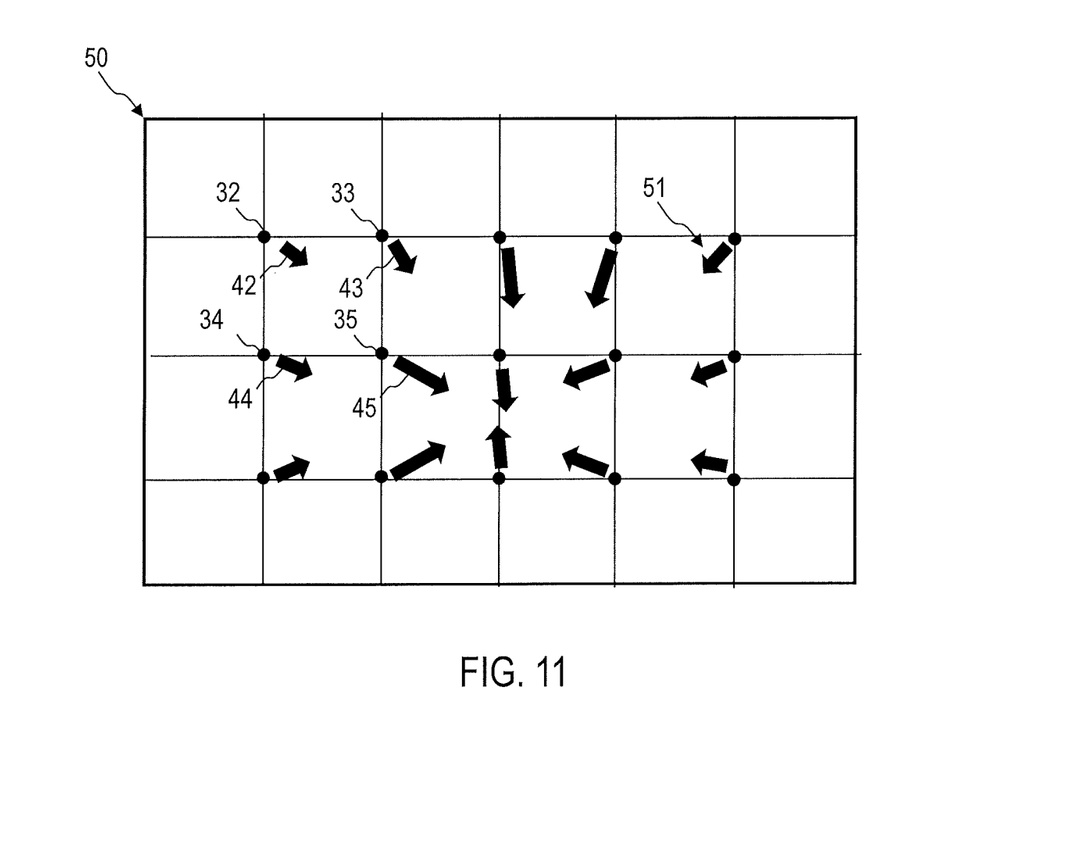
FIG. 11 shows processing of detected Raman spectra by a device according to an embodiment.

FIG. 11 shows as an example the determination of a gradient field 50. For multiple sites in the tissue sample, the gradient field 50 indicates the strength, and optionally the direction of movement, of the intensity of a Raman peak 41-43 or a plurality of Raman peaks 41-43 characteristic of aggressive prostate tumors. The plurality of gradients 51 can provide one piece of data in each case on the strength of the decrease or increase in the intensity of the Raman peaks 41-43, which is indicated in FIG. 11 by the length of the corresponding arrow. The plurality of gradients 51 can provide one piece of data in each case on the direction of the decrease or increase in the intensity of the Raman peaks 41-43, which is indicated in FIG. 11 by the direction of the corresponding arrow.

The gradients 42-45 shown as an example can be calculated from the intensity or the spectral weight of Raman peaks 41-43 for biomarkers of the malignant prostate tumor. As schematically shown in FIG. 11, the gradients provide data on the position of the tumor.

The gradients 51 need not be determined based on the intensities of the Raman peaks 41-43. For example, the gradients 51 can also be determined for the distance 125 shown by the data points in a statistical analysis of the areas 103, 104 in the data space to which aggressive or non-aggressive prostate tumors are assigned.

Various techniques can be used to determine the intensity gradients or the spectral weight of Raman peaks in a spatially resolved manner. For example, for an area with coordinates (x,y), one can determine the gradient 51 according to $$\vec{g}(x, y) = \begin{pmatrix} [(I(x+\Delta x, y) - I(x, y)]/\Delta x \\ [(I(x, y+\Delta y) - I(x, y)]/\Delta y \end{pmatrix} \quad (1)$$

wherein data detection in two dimensions was taken as an example. In equation (1), g denotes the determined gradients. Here, I(x,y) denotes the intensity or the spectral weight of a Raman peak characteristic of an aggressive or non-aggressive prostate tumor at coordinates (x,y). I(x+Δx, y) denotes the intensity or the spectral weight of the same Raman peak at coordinates (x+Δx, y). I(x, y+Δy) denotes the intensity or the spectral weight of the same Raman peak at coordinates (x, y+Δy).

For the detection of Raman spectra on a regular, e.g. a rectangular grid, as shown by way of example in FIG. 2 by the reference number 30, the gradient can be determined as $$\vec{g}(x, y) = \begin{pmatrix} [(I(x+a_x, y) - I(x-a_x, y)]/[2a_x] \\ [(I(x, y+a_y) - I(x, y-a_y)]/[2a_y] \end{pmatrix} \quad (2)$$

where $a_x$ is the distance between adjacent data detection points along one coordinate axis and $a_y$ is the distance between adjacent data detection points along a further coordinate axis orthogonal thereto.

In a determination of the gradients based on the results of a statistical analysis, e.g. a principal component analysis, the corresponding equations (1) and (2) can also be used, wherein instead of I(x,y), the respective distance 125 of the Raman spectrum/spectra that can be detected at the corresponding site in the data space of the principal component analysis can be used.

The position and also the aggressiveness of a malignant prostate tumor can be determined even if no cancer cells are present in the sample 9 itself. For this purpose, the presence or optionally also the spatial change in Raman peaks, or the results of the statistical analysis of a plurality of Raman spectra as a function of the distance from the prostate, are used.

Figure 12:
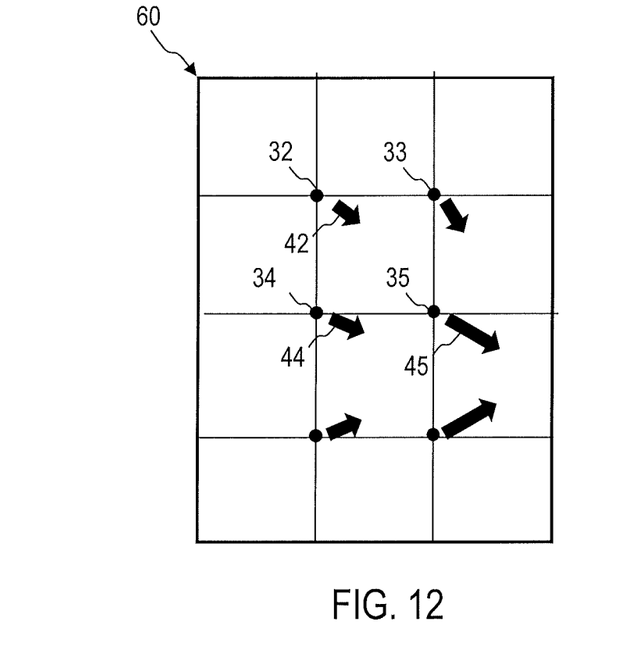
FIG. 12 shows processing of detected Raman spectra by a device according to an embodiment.

FIG. 12 is a schematic diagram of a gradient field 60 which is automatically determined by the evaluation unit 20 and which indicates the site-dependent change in intensity, the spectral weight of the Raman peaks 41-43, or the distances 125 from the area 103 that are characteristic of aggressive prostate tumors. Even if the tumor is not contained in the sample, its location can be estimated based on the course of the local change in intensity or the spectral weight of the Raman peaks 41-43. Alternatively or additionally, the change in intensity or the spectral weight of the Raman peaks, which is determined from the sample, can be extrapolated so that the intensity or the spectral weight of the corresponding Raman peaks at a site of the prostate tumor that is no longer contained in the sample can be estimated. This can be used for assessment of the prostate tumor and/or stage determination.

Similar methods can also be used for the analysis of biopsy specimens, which for example are obtained by punch biopsy.

Figure 13:
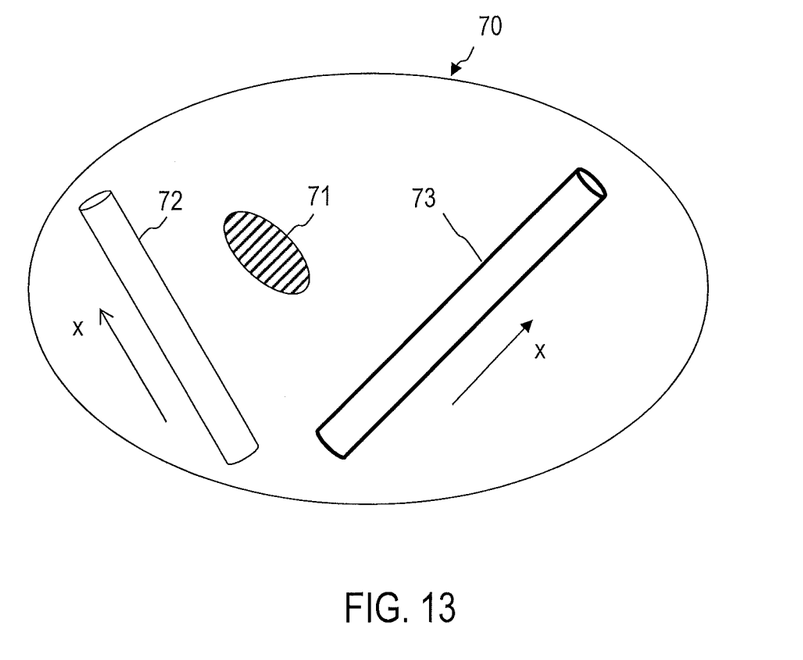
FIG. 13 shows the position of samples obtained by punch biopsy, which are evaluated by a device according to an embodiment.

FIG. 13 is a diagram 80 illustrating the position of biopsy specimens 72, 73 obtained by punch biopsy. The biopsy specimens 72, 73 can contain cells of a malignant prostate tumor 71. However, the biopsy specimens 72, 73 can also be in a position such that they contain no cells of the malignant prostate tumor 71. The biopsy specimens 72, 73 can contain prostatic stromal cells.

The evaluation unit 20 can detect respective Raman spectra at multiple sites along the biopsy specimens 72, 73. Based on the presence of Raman peaks assigned to prostate cancer, it can be concluded that a malignant prostate tumor is present. Alternatively or additionally, further data can be obtained from the local change in Raman peaks assigned to the prostate cancer. For example, it can be concluded that the prostate tumor is aggressive based on the local change in the intensity and/or the spectral weight of Raman peaks for biomarkers indicating the malignant prostate tumor.

Identification of the aggressiveness of the prostate tumor need not be carried out based on individual Raman peaks, but can also be carried out based on a statistical analysis of one or a plurality of Raman spectra together. Prior knowledge of the assessment of Raman wavenumbers and biomarkers is not required.

Figure 14:
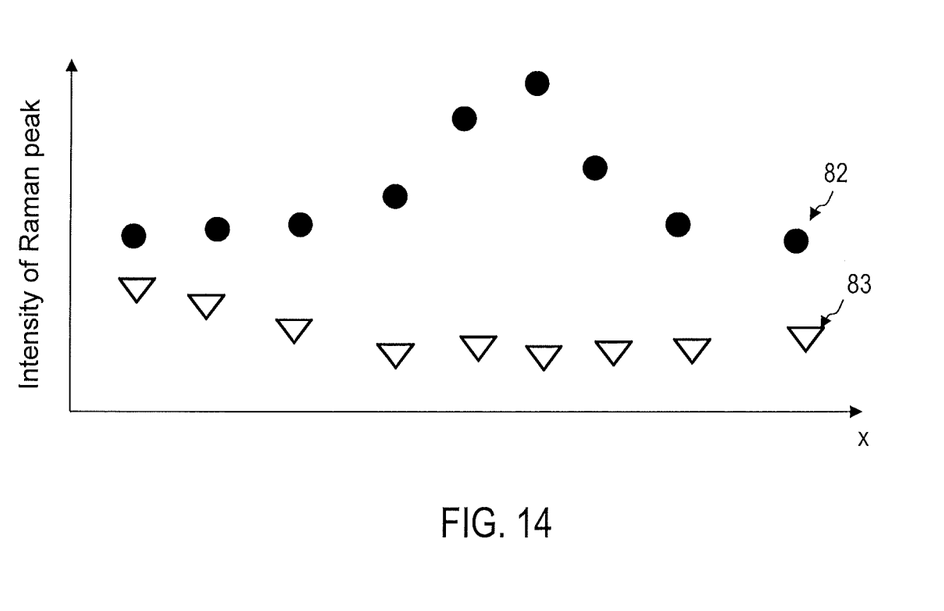
FIG. 14 shows processing of detected Raman spectra by a device according to an embodiment.

FIG. 14 shows as an example the intensity of a Raman peak, which for example can be a Raman peak of a genetic or molecular biomarker for prostate cancer, as a function of the site for the biopsy specimen 72 (data 82) and the biopsy specimen 73 (data 83). The spatial change in intensity shown can be evaluated in order to determine the amount of the corresponding biomarker, for example, present in the prostate tumor itself. The aggressiveness of the malignant prostate tumor can be calculated.

The electronic evaluation unit can be configured to determine the aggressiveness of the prostate tumor based on the detected Raman spectrum, for example based on a characteristic pattern of the Raman spectrum at one or a plurality of wavenumbers or wavenumber ranges.

Identification of the aggressiveness of the prostate tumor need not be carried out based on individual Raman peaks, but can also be carried out based on a statistical analysis of one or a plurality of Raman spectra as a whole. Prior knowledge of the assessment of Raman wavenumbers and biomarkers is not required.

In this manner, one or a plurality of patterns in the position, height, and flank steepness defined by a Raman spectrum and a combination of a plurality of Raman peaks are used to make assessments of the presence and/or aggressiveness of a prostate tumor. The pattern in a Raman spectrum can be defined by one or a plurality of parameters selected from the group composed of the wavenumbers at which the Raman peaks are located, the peak heights, the flank steepness of the peaks, the distances between the peaks, and/or combinations of peaks in one or a plurality of Raman spectra.

Figure 15:
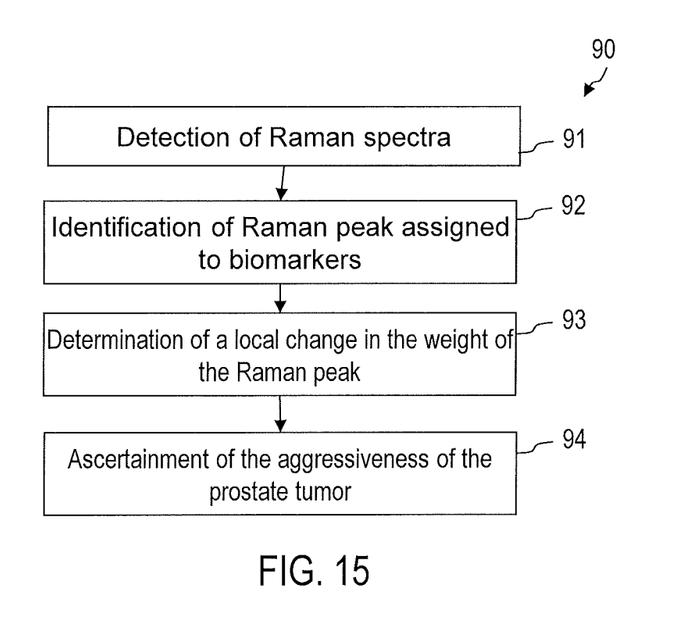
FIG. 15 is a flow diagram of a method according to an embodiment.

FIG. 15 is a flow diagram of a method 90 according to an embodiment.

In step 91, at least one Raman spectrum of the sample 9 is detected. The light source 11 is controlled in such a way that an excitation beam 17 is produced. A plurality of Raman spectra can also be detected. For example, a plurality of Raman spectra can be detected at different sites in the same sample or in different samples in order to identify a malignant prostate tumor.

In step 92, the evaluation device 20 evaluates the detected Raman spectrum. The evaluation device 20 can identify at least one Raman peak which is characteristic of a biomarker indicative of prostate cancer.

In step 93, a spatial change in at least one Raman peak which is characteristic of a biomarker indicative of prostate cancer can optionally be calculated.

In step 94, it is automatically determined whether a malignant prostate tumor is present depending on the evaluation of the at least one Raman spectrum. The aggressiveness and/or stage of the prostate tumor can be automatically determined.

In devices and methods according to the illustrative embodiments described, the evaluation of Raman spectra can comprise a comparison with each of the Raman peaks of biomarkers indicative of aggressive or non-aggressive prostate tumors.

By means of devices and methods, a biomarker or a plurality of biomarkers, which are selected from a group composed of AMACR, FOLH1 (PSMA), PTEN, PCA3, ERG3 and PSA, can be identified by Raman spectroscopy. Spatially resolved determination of the change in the corresponding Raman peaks can be carried out in order to identify the prostate tumor and optionally to determine whether or not the prostate cancer is aggressive.

Alternatively or additionally, the reaction of prostate cells, stroma cells, or other components of the sample to the substances produced by a prostate tumor can be determined. In this manner, a conclusion can be drawn as to the presence of a prostate tumor and/or differentiation of aggressive and non-aggressive prostate tumors can be carried out.

Devices and methods according to illustrative embodiments can generally be used for the quantitative analysis of samples for identifying prostate tumors. The devices and methods can be used in particular for the analysis of previously obtained samples, with the production of the samples not being included within the scope of the analysis methods.

The invention claimed is:

1. A device for identifying a prostate tumor, comprising:
a Raman spectroscopy system for the detection of a plurality of Raman spectra of a tissue sample; and
an electronic evaluation unit which is configured to identify the prostate tumor depending on an evaluation of the plurality of Raman spectra;
wherein the Raman spectroscopy system is configured to detect, at a plurality of positions of the tissue sample, the plurality of Raman spectra;
wherein the electronic evaluation unit is configured to evaluate the plurality of Raman spectra detected at the plurality of positions of the tissue sample, to determine a gradient field by evaluating the plurality of Raman spectra in order to determine the position of the prostate tumor in the tissue sample or relative to the tissue sample; and wherein the gradient field for the plurality of Raman spectra detected at the plurality of positions indicates how strongly and in which direction an intensity of a Raman peak or several Raman peaks changes.

2. The device as claimed in claim 1, wherein the electronic evaluation unit is configured to determine whether an aggressive or non-aggressive prostate tumor is present by means of a statistical evaluation of the plurality of Raman spectra.

3. The device as claimed in claim 2, wherein the electronic evaluation unit is configured to determine whether the aggressive or non-aggressive prostate tumor is present by means of a principal component analysis or a cluster analysis of the plurality of Raman spectra.

4. The device as claimed in claim 1, wherein the electronic evaluation unit is configured to identify Raman peaks and characteristic patterns in the plurality of Raman spectra that are characteristic of an aggressive prostate tumor or a non-aggressive prostate tumor by evaluating the plurality of Raman spectra.

5. The device as claimed in claim 1, wherein the electronic evaluation unit is configured to determine a local change in a Raman signal which is characteristic of an aggressive prostate tumor or a non-aggressive prostate tumor from the plurality of Raman spectra detected at multiple sites.

6. The device as claimed in claim 5, wherein the electronic evaluation unit is configured to determine a gradient of an intensity and/or a spectral weight of the Raman signal in a spatially resolved manner.

7. The device as claimed in claim 1, wherein the electronic evaluation unit is configured to compare the plurality of Raman spectra detected at one site or the multiple sites with data on stored reference spectra.

8. The device as claimed in claim 1, wherein the device is configured to detect at least some of the plurality of Raman spectra detected at the multiple sites in various subcellular structures of prostate tissue cells.

9. The device as claimed in claim 1, wherein the tissue sample is a histological section of one or a plurality of prostate punch biopsy specimens.

10. The device as claimed in claim 1, wherein the tissue sample is one or a plurality of histological sections from one or more parts of a surgically removed prostate.

11. The device as claimed in claim 1, wherein the evaluation device is configured to compare Raman spectra detected in the sample with reference spectra in order to determine the aggressiveness or non-aggressiveness of the prostate tumor.

12. The device as claimed in claim 1, wherein the electronic evaluation unit is configured to determine the aggressiveness of the prostate tumor by evaluating the plurality of Raman spectra.

13. A method for evaluating a tissue sample for the identification of a prostate tumor, comprising:
detecting a plurality of Raman spectra of the tissue sample; and
identifying the prostate tumor by evaluating the plurality of Raman spectra;
wherein detecting of the plurality of Raman spectra comprises:
detecting the plurality of Raman spectra at multiple sites in the tissue sample, and
wherein evaluating of the plurality of Raman spectra comprises:
determining a gradient field for the plurality of Raman spectra at the multiple sites;
indicating from the gradient field how strongly and in which direction an intensity of a Raman peak or several Raman peaks changes; and
determining a position of the prostate tumor in the tissue sample or relative to the tissue sample from the changes in the intensity of the Raman peak or several Raman peaks.

14. The method as claimed in claim 13, further comprising:
determining a distribution of at least one biomarker based on the plurality of Raman spectra detected at the multiple sites;
determining the site of the prostate tumor in the tissue sample or relative to the tissue sample using the determined distribution of the at least one biomarker; or
determining an aggressiveness of the prostate tumor using the determined distribution of the at least one biomarker.

15. The method as claimed in claim 13, further comprising:
performing a statistical evaluation of the plurality of Raman spectra utilizing a principal component analysis or a cluster analysis.

16. The method as claimed in claim 13, further comprising:
determining the aggressiveness of the prostate tumor using the evaluation of the plurality of Raman spectra detected at the multiple sites.

* * * * *